US006475989B1

(12) United States Patent
Sattin et al.

(10) Patent No.: US 6,475,989 B1
(45) Date of Patent: Nov. 5, 2002

(54) USE OF PYROGLUTAMYL-GLUTAMYL-PROLYL AMIDE (EEP) FOR NEUROLOGICAL AND NEUROBEHAVIORAL DISORDERS

(76) Inventors: Albert Sattin, 1811 Barry Ave., Los Angeles, CA (US) 90025; Albert E. Pekary, 4022 Globe Ave., Culver City, CA (US) 90230; Robert L. Lloyd, 1533 Fern Ave., Duluth, MN (US) 55805

( * ) Notice: Subject to any disclaimer, the term of this patent is extended or adjusted under 35 U.S.C. 154(b) by 0 days.

(21) Appl. No.: 09/169,657

(22) Filed: Oct. 9, 1998

Related U.S. Application Data

(60) Provisional application No. 60/062,142, filed on Oct. 9, 1997.

(51) Int. Cl.$^7$ .......................... A61K 38/06; C07K 5/093

(52) U.S. Cl. ........................................ 514/18; 530/331

(58) Field of Search .............................. 514/18; 530/331

(56) References Cited

U.S. PATENT DOCUMENTS

| | | | | |
|---|---|---|---|---|
| 3,737,549 A | * | 6/1973 | Plotnikoff | 424/274 |
| 3,932,623 A | * | 1/1976 | Wilson | 424/177 |
| 4,608,365 A | | 8/1986 | Engel | |
| 4,788,179 A | | 11/1988 | Flohe et al. | |
| 4,906,614 A | | 3/1990 | Giertz et al. | |
| 5,244,884 A | | 9/1993 | Spatola et al. | |

OTHER PUBLICATIONS

File Caplus on STN. DN No. 121:100276. Ashworth et al. J. Endocrinol. (1994), 142(1), pp. 111–118. Abstract only.*
Mabrouk, et al. 'Evaluation of the Behavioural Effects of a Novel Thyrotrophin–Releasing Hormone (TRH)–Like Peptide (pGlu–Glu–ProNH2, EEP), in the Rat', British Journal of Pharmaceology, 1993, 178p, vol. 110. Abstract only.*
Patel et al. 'Pharmacotherapy of Cognitive Impairment in Alzheimer's Disease:A Review', J. Geriatr. Psychiatry. Nurol. vol. 8, pp. 81–85, 1995.*
The Merck Manual, Sixth Edition, published 1992 by Merck Research Labratories, pp. 1464–1465 and 1511–15–13, 1995.*
Akinsanya, K.O., et al, "Gonadal steroids regulate rat anterior pituitary levels of TSH–releasing hormone– and pyroglutamyl–glutamyl–proline amide–like immunoreactivity", Endocrinology, 1995, 734–740, vol. 136, Issue 2 [ABSTRACT].
Akinsanya, K.O., et al., "In vivo and in vitro effects of dexamethasone on pituitary thyrotrophin–releasing hormone–like peptide concentrations in the rat", Journal of Endocrinology, 1995, 333–341, vol. 145, Issue 2 [ABSTRACT].

Callahan, A.M., et al., "Comparative Antidepressant Effects of Intravenous and Intrathecal Thyrotropin–Releasing Hormone: Confounding Effects of Tolerance and Implications for Therapeutics", Biological Psychiatry, 1997, 264–272, vol. 41.
Klootwijk, W., et al., "High serum levels of the thyrotropin–releasing hormone–like peptide pyroglutamyl–glutamyl–prolineamide in patients with carcinoid tumors", Journal of Clinical Endocrinology & Metabolism, 1996, 2816–2820, vol. 81, Issue 8 [ABSTRACT].
Klootwijk, W., et al., "Urinary excretion of the TRH–like peptide proglutamyl–glutamyl–prolineamide in rats", Journal of Endocrinology, 1997, 411–421, vol. 153, Issue 3 [ABSTRACT].
Lloyd, R.L., et al., "Antidepressant Effects of a Stable Analogue of Thyrotropin Releasing Hormone in a Rodent Model of Depression", Society for Neuroscience Abstracts, Oct. 25–30, 1997, 1661, vol. 23, Part 2.
Mabrouk, M.M., et al., "Evaluation of the behavioural effects of a novel thyrotropin–releasing hormone (TRH)–like peptide (pGlu–Glu–ProNH–2, EEP) in the rat", British Journal of Pharmacology, 1993, 178P, vol. 110 [ABSTRACT].
Marangell, L.B., "Effects of Intrathecal Thyrotropin–Releasing Hormone (Protirelin) in Refractory Depressed Patients", Arch Gen Psychiatry, Mar., 1997, 214–222, vol. 54.
Ogawa, N., et al., "Potential Anti–depressive Effects of Thyrotropin Releasing Hormone (TRH) and Its Analogues[1]", Peptides, 1984, 743–746, vol. 5.
O'Leary, R., et al., "Thyrotropin–Releasing Hormone", Journal of Neurochemistry, 1995, 953–963, vol. 65, No. 3.
Pekary, A.E., et al., "Electroconvulsive seizures increase levels of pGlu–Glu–Pro–NH$_2$ (EEP) in rat brain", Peptides, 1999, 107–119, vol. 20.
Pekary, A.E., et al., "Electroconvulsive Seizures (ECS) Increase pGLU–GLU–PRO–NH$_2$ (EEP) Levels in Rat Limbic System", Society for Neuroscience Abstracts, Oct. 25–30, 1997, 2377, vol. 23, Part 2.
Pekary, A.E., et al., "Predominance of pGlu–His–Pro–Gly among All TRH Precursor Peptides in Rat Limbic Forebrain after Electroconvulsive Seizures[α]", Annals New York Academy of Sciences, 1994, 330–333, vol. 739.

(List continued on next page.)

*Primary Examiner*—Christopher S. F. Low
*Assistant Examiner*—Anish Gupta
(74) *Attorney, Agent, or Firm*—Stephen A. Slusher; Deborah A. Peacock; Jeffrey D. Myers

(57) ABSTRACT

A tri-peptide drug for treatment of neurological and neurobehavioral disorders of a mammal, such drug being derived from the following formula: pGlu-X-Pro-NH$_2$, wherein the internal amino acid (X) is a non-histadine amino acid. Methods of treatment of neurological disorders using the tri-peptide, including as an adjunct, synergist or stand-alone therapy, in oral, parenteral, intranasal, transcutaneous, or rectal forms.

6 Claims, 3 Drawing Sheets

OTHER PUBLICATIONS

Rondeel, J.M.M., et al., "Further studies on the regulation, localization and function of the TRH–like peptide pyroglutamyl–glutamyl–prolineamide in the rat anterior pituitary gland", *Journal of Endocrinology*, 1995, 293–300, vol. 146, Issue 2 [ABSTRACT].

Rondeel, J.M.M., et al., "Regulation of the TRH–like peptide pyroglutamyl–glutamyl–prolineamide in the rat anterior pituitary gland", *Journal of Endocrinology*, 1995, 43–49, vol. 145, Issue 1 [ABSTRACT].

Sattin, Albert, et al., "TRH Gene Products Are Implicated in the Antidepressant Mechanisms of Seizures$^{ca}$", *Annals New York Academy of Sciences*, Oct. 31, 1994, 135–153, vol. 739.

Stern, R.A., et al., "Antidepressant and Memory Effects of Combined Thyroid Hormone Treatment and Electroconvulsive Therapy: Preliminary Findings", *Biological Psychiatry*, 1991, 623–627, vol. 30.

Akinsanya, K.O., et al, "Gonadal steroids regulate rat anterior pituitary levels of TSH–releasing hormone– and pyroglutamyl–glutamyl–proline amide–like immunoreactivity", *Endocrinology*, 1995, 734–740, vol. 136, Issue 2, The Endocrine Society.

Akinsanya, K.O., et al., "In vivo and in vitro effects of dexamethasone on pituitary thyrotrophin–releasing hormone–like peptide concentrations in the rat", *Journal of Endocrinology*, 1995, 333–341, vol. 145, Issue 2, Great Britain.

Horita, A., "An Update on the CNS Actions of TRH and Its Analogs", *Life Sciences*, 1998, 1443–1448, vol. 52, Nos. 17/18, Elsevier Science, Inc.

Klootwijk, W., et al., "High serum levels of the thyrotropin–releasing hormone–like peptide pyroglutamyl–glutamyl–prolineamide in patients with carcinoid tumors", *Journal of Clinical Endocrinology & Metabolism*, 1996, 2816–2820, vol. 81, Issue 8, The Endocrine Society.

Klootwijk, W., et al., "Urinary excretion of the TRH–like peptide proglutamyl–glutamyl–prolineamide in rats", *Journal of Endocrinology*, 1997, 411–421, vol. 153, Issue 3, Great Britain.

Mabrouk, M.M., et al., "Evaluation of the behavioural effects of a novel thyrotropin–releasing hormone (TRH)–like peptide (pGlu–Glu–ProNH–2, EEP) in the rat", *British Journal of Pharmacology*, 1993, 178P, vol. 110.

O'Leary, R., et al., "Thyrotropin–Releasing Hormone", *Journal of Neurochemistry*, 1995, 953–963, vol. 65, No. 3, Lippincott–Raven Publishers, Philadelphia.

Rondeel, J.M.M., et al., "Further studies on the regulation, localization and function of the TRH–like peptide pyroglutamyl–glutamyl–prolineamide in the rat anterior pituitary gland", *Journal of Endocrinology*, 1995, 293–300, vol. 146, Issue 2, Great Britain.

Rondeel, J.M.M., et al., "Regulation of the TRH–like peptide pyroglutamyl–glutamyl–prolineamide in the rat anterior pituitary gland", *Journal of Endocrinology*, 1995, 43–49, vol. 145, Issue 1, Great Britain.

Sattin, A., "The Role of TRH and Related Peptides in the Mechanism of Action of ECT", *The Journal of ECT*, 1999, 76–92, vol. 15, No. 1, Lippincott Williams & Wilkins, Inc., Philadelphia.

* cited by examiner

USE OF PYROGLUTAMYL-GLUTAMYL-PROLYL AMIDE (EEP) FOR NEUROLOGICAL AND NEUROBEHAVIORAL DISORDERS

CROSS-REFERENCE TO RELATED APPLICATIONS

This application claims the benefit of the filing of U.S. Provisional Patent Application Ser. No. 60/062,142, entitled *A Method for Treating, Diagnosing and Clinically Assessing Neurobehavioral Disorders with Pyroglutamyl-Glutamyl-Prolyl Amide (EEP)*, filed on Oct. 9, 1997, and the specification thereof is incorporated herein by reference.

BACKGROUND OF THE INVENTION

1. Field of the Invention (Technical Field)

The present invention relates to the potential therapeutic use of the naturally occurring biologic tri-peptide pyroglutamyl-glutamyl-prolyl amide ("EEP"), and any and all peptide and protein analogues thereof. Included in the invention are the class of tri-peptides with $NH_2$-terminal pyroglutamyl- and COOH-terminal prolyl amide, but with variable internal amino acids; that is, where the internal glutamate has been substituted for some other internal amino acid or the analogues thereof with the exception of histidine and its analogues. The invention includes any chemical derivatives of EEP which elicit any of the physiological or therapeutic effects of EEP.

2. Background Art

Pyroglutamyl-glutamyl-prolyl amide ("EEP") is a naturally occurring biologic tri-peptide found in the blood and internal organs of animals, including humans. EEP is synthesized naturally in the brain, and possibly other organs from the cleavage of a larger protein or peptide. However, this precursor protein is different from the well-characterized precursor of thyrotropin-releasing hormone "TRH"). The TRH precursor, prepro-TRH, has been fully sequenced, and the EEP sequence is not present within prepro-TRH. Similar to TRH, the EEP peptidergic system occurs within the limbic system neurons in the central nervous system ("CNS"), and the amounts of each increase following seizures. See, Lloyd et al., *Society for Neuroscience Abstracts*, Vol. 23(Part 2), p.1661, 1997; Pekary et al., *Society for Neuroscience Abstracts*, Vol. 23(Part 2), p.2377, 1997; Sattin et al., *Annals NY Academy of Science*, Vol. 739, pp. 135–153, 1997, and Pekary et al., "Electroconvulsive seizures increase levels of pGlu-Glu-Pro-$NH_2$. (EEP) in rat brain", Peptides, 1999, the teachings of which are hereby incorporated by reference.

TRH has been shown to produce marked improvement in neurological and neuromuscular functions associated with both lower and upper neurons. See, Engle, U.S. Pat. No. 4,608,365. For example, when given to patients with amyotrophic lateral sclerosis, TRH produced a marked improvement of functions of both lower and upper neurons. However, because of the instability of TRH in the blood, the beneficial effects last from only one to 24 hours and high doses are required (0.71 mg/kg of body weight, once or twice per day) depending upon the patient. Accordingly, TRH is generally administered by continuous intravenous infusions in high doses, and only in exceptional cases is intramuscular or peroral administration considered. See, Geirtz et al., U.S. Pat. No. 4,906,614. Attempts have been made to synthesize chemical analogues of the TRH molecule that have the biological properties of TRH but which are stable toward metabolizing enzymes. For example, O'Leary et.al, reports in Journal of Neurochemistry, Vol. 65, No. 3, pp. 953–63 that a methyl substituted histidyl analogue of TRH is less prone to metabolic degradation. Other examples include the report of Giertz who substituted the C-terminus of TRH, i.e., pyroglutamyl moiety, for a cyclic organic moiety, and Spattola et al., U.S. Pat. No. 5,244,884 who reported a thionated analogue of TRH whereby at least one of the four carbonyl oxygens was substituted with sulfur. One distinguishing feature of all these TRH analogues, in relation to the present invention, is that they all bind to TRH receptor sites within the brain. In contrast, EEP although exhibiting TRH-like physiological effects, does not bind with TRH-receptors. The present invention however is not limited by this physiological relationship, since some of the chemical analogues of EEP may interact with TRH receptors to some extent.

EEP differs from TRH in that the middle amino acid is glutamate instead of histidine. This structural difference is significant because the absence of the histidine residue in the former precludes digestion of the tri-peptide by pyroglutamate aminopeptidase 11 ("PAP II"). PAP II is known to hydrolyze only tri-peptides containing N-terminal pyroglutamate and with histidine in the penultimate position.

Like TRH, EEP is shown to be an effective antidepressant in the highly predictive rat Forced-swim test. However, because EEP has a longer half-life under physiological conditions, its potency in the rat Forced-swim test might be as high as forty fold greater than that of TRH. In addition, EEP occurs naturally in the blood as well as in the brain, and more importantly it is not significantly metabolically degraded in the blood. Thus, in contrast to the recent attempts to utilize TRH to treat depression, treatment with EEP, in accordance with the present invention, can be applied as a practical alternative. For example, EEP can be administered intravenously, subcutaneously or orally, while TRH requires invasive injection into the spinal fluid. See, Callahan et al., Biological Psychiatry, Vol. 41, pp.263–272, 1997, Marangell et al., in *Archives of General Psychiatry*, Vol. 54, pp. 214–222, 1997. In the reports by Callahan et al., and Marangell et al., patients with depression responded with improvement to 500 micrograms (0.5 milligram) TRH.

SUMMARY OF THE INVENTION
(DISCLOSURE OF THE INVENTION)

The present invention is a drug for treatment of neurological and neurobehavioral disorders of mammals, including humans. The drug comprises a tri-peptide comprised of an N-terminal pyroglutamyl moiety, a C-terminal prolyl amide moiety, and an internal amino acid or analogue thereof.

In one embodiment, the internal amino acid comprises an amino acid other than histidine or its analogues. In another embodiment, the amino acid(s) comprises glutamate or phenylalanine.

The present invention is also a method of treating neurological and neurobehavioral disorders of mammals by administering the tri-peptide to a mammal.

The invention also includes methods of administering the tri-peptide to a mammal that result in improvements in the following disorders: neuromuscular weakness, spinal cord trauma, spasticity, schizophrenia, dementias, Alzheimer's, somatization disorders, psychosomatic disorders, functional bowel disorders, epileptic disorders, sleep disorders, and loss of motoric or cognitive functions resulting from spinal cord or brain stem injuries.

The invention includes the following modes of administration: oral, parenteral, intranasal, transcutaneous, and rectal.

The invention also includes a method to detect and assay the tri-peptide, which includes subtracting the amount of tri-peptide containing an internal histidine or histidine analogue from the total amount of TRH-like tri-peptide present in the blood or tissue sample.

The use of the present invention is for the treatment of various neurological and neurobehavioral disorders in humans and any form of animal life for which the licensed health practitioner or veterinarian deems such treatment appropriate.

Primary object of the present invention is to provide pharmaceutical compositions of the present invention for use in the above-mentioned treatments.

A primary advantage of the present invention is the relatively high metabolic stability of EEP in the blood.

Another advantage of the present invention is that it maintains high levels of efficacy under different modes of administration, and may be combined with many different treatments without adverse effect.

Another major advantage of the present invention is the unprecedented rapid onset of the therapeutic effect, within one day, or within hours, in contrast with all established previous treatments which (e.g. in the case of depression) require weeks.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

A BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

Figure 1:
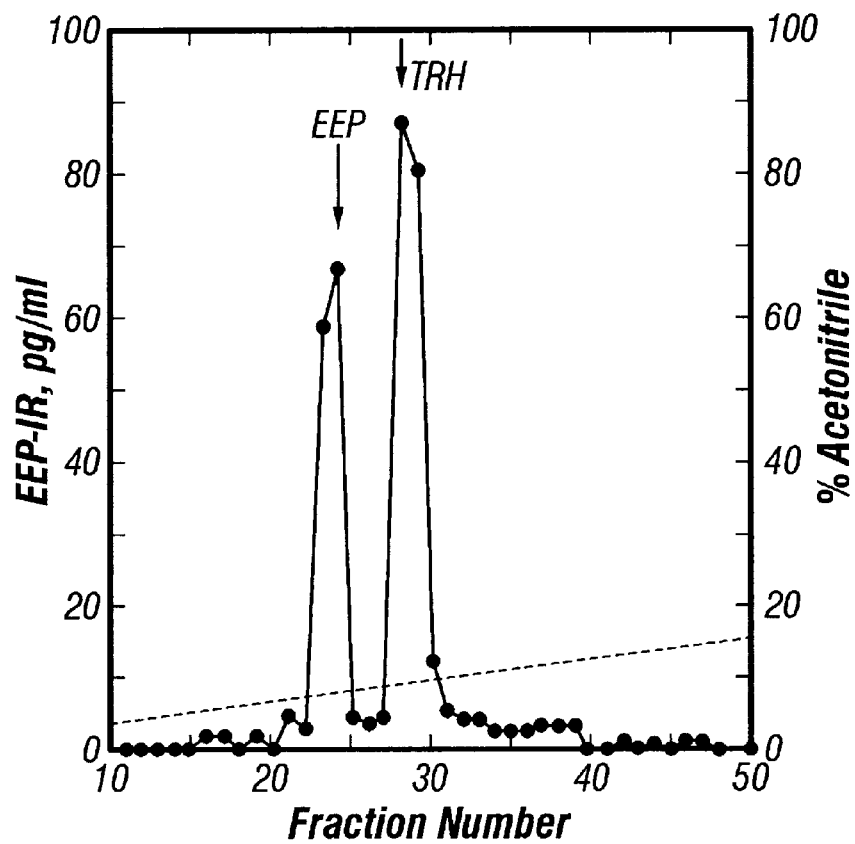
FIG. 1 is a graph showing HPLC and EEP-RIA of pooled extracts of pyriform cortex from electroconvulsive seizure (ECS) treated rats.

DESCRIPTION OF THE PREFERRED EMBODIMENTS (BEST MODES FOR CARRYING OUT THE INVENTION)

The present invention includes any and all peptides and protein precursors and analogs of EEP. The preferred compounds are those corresponding to the following chemical formula:

pGlu-Glu-Pro-NH$_2$.

The composition must include the NH$_2$-terminal pyroglutamyl- and COOH-terminal prolyl amide, along with an internal amino acid. The internal amino acid in EEP is glutamate, but may be substituted by any other non-histamine-derived amino acid (pGlu-X-Pro-NH$_2$), wherein X is a non-histamine-derived amino acid. For example, another natural biological tripetide, EFP (pyroglutamyl-phenylalanyl-prolyl amide) has similar therapeutic effects as EEP. The invention also includes any chemical derivatives of EEP which elicit any of the physiological or therapeutic effects of EEP.

Also included in the present invention are the potential therapeutic uses of any and all peptide and protein precursors of EEP. EEP is administered as a drug by any route whatsoever, including but not limited to oral and parenteral routes, for the treatment of any or all neurobehavioral disorders. Treatment includes all humans and any form of animal life for which the licensed health practitioner or veterinarian deems such treatment appropriate. The categories of conditions to be treated include, but are not limited to, the affective disorders (including mood and anxiety disorders), schizophrenia, dementias, (including Alzheimer's disease), somatization disorders, spasticity, psychosomatic disorders, including functional bowel disorders, epileptic disorders, neuromuscular weakness, and sleep disorders. Any disorder of the central nervous system that is believed to be associated with an imbalance of the neuronal circuitry described by A. Sattin Journal ECT, 1999, the teachings of which are hereby incorporated by reference, may be the object of such treatment. Also, like TRH and its analogues, EEP can be used in the recovery of the motoric and cognitive function following spinal cord trauma or brain stem injuries.

In an alternative embodiment, EEP is used in combination with electroconvulsive therapy ("ECT") for the treatment of a variety of mental and behavioral disorders. At present, ECT is the most effective treatment for depression, but prior antidepressant drugs usually are not used in conjunction with such treatment. In humans, current antidepressant drugs afford no synergistic benefit at all when given with ECT. In fact, package inserts provided by most antidepressant drug manufacturers recommend not using such products in conjunction with ECT. Regarding the present invention, the effect of EEP on ECT is distinctly different from all established antidepressant drugs. EEP acts synergistically with ECT by potentiating the beneficial effects of ECT. Like EEP, TRH is also known to mediate ECT. However, the latter must be injected directly into the spinal fluid, and because of the relatively short half-life, the effects of TRH last only 1–2 days.

Other peptides with known antidepressant and other therapeutic neurological properties, such as TRH, are more easily metabolized in the body. Hence large doses are required and administration of the peptide drug is often problematic. In contrast, EEP has been shown to be effective at doses as low as 0.5 microgram per kilogram, and can be administered by many different modes.

The peptide can be administered orally. Oral administration may include liquid, suspension, tablet and capsule form, utilizing, for example, various aqueous vehicles, flavors, colors or capsule formulations. A parenteral form may be provided in a type of buffered solution, and with biologically compatible antioxidants and/or preservatives. Intranasal applications could utilize known aqueous or liquid solutions. The compound may also be administered transcutaneously.

The above forms of the compound and modes of administration are based upon each patient's particular disease and dosage requirements.

Since EEP is believed to function through a mechanism that differs from any of the established antidepressant drugs, the concomitant use of any of the antidepressant drugs is also within the scope of the use of EEP in selected cases. For example, the thyroid hormone T3 (liothyronine) has been shown to speed up the antidepressant effects of the antidepressant drugs, or to convert a non-responder to a responder. Stern et al., in *Biological Psychiatry*, Vol. 30, No. 6, pp. 623–27, reported that 50 micrograms of T3 given at bedtime significantly reduced the required numbers of ECTs from 12 to 7. Since EEP works cooperatively with ECT some patients benefit from the co-administration of the thyroid hormone T3. The potentiative interaction with thyroid hormones is of value in some cases in which the desired response is not obtained with EEP alone.

In an alternative embodiment, physiological levels of EEP are used as a preliminary chemical determination of depression or to monitor its treatment. For example, the amount of EEP in blood, other body fluids, or organs, in comparison with a reference standard, can be used by the health practitioner or veterinarian for the diagnosis or treatment of neurobehavioral disorders. A series of blood determinations of EEP is used to assist a physician in determining the adequacy of treatment of the condition. For example, regular checks of blood level expedite determination of the appropriate dose of EEP for each individual, or determine the reason for ineffectual results.

The assay for EEP allows one to accurately measure its concentration in brain tissue, blood or any body fluid. The antiserum, which measures EEP also, measures any TRH which may be co-present. TRH and EEP are the only TRH-like peptides that occur in rat brain tissue. Thus, by measuring TRH separately via a highly specific TRH RIA, the EEP concentration is determined as the difference of the two measurements.

EXAMPLES

More direct evidence for the validity of the above-described subtraction procedure was obtained by comparing the profiles resulting from the simultaneous EEP and TRH RIA of HPLC of pooled tissue extracts. The EEP RIA results for the pooled pyriform cortex of rats in the ECS treatment group are displayed in FIG. 1. The corresponding TRH RIA results were nearly superimposable except that the peak corresponding to EEP was completely missing (result not shown). See Pekary et al., "Electroconvulsive seizures increase levels of pGlu-Glu-Pro-NH$_2$ (EEP) in rat brain", Peptides, 1999, which is incorporated herein by reference.

The effectiveness of EEP on depression can be seen from the following examples in animal models.

Example 1

The Porsolt forced-swim test (FST) is well documented as an animal model of antidepressant effects. All clinically effective antidepressant drugs are positive in this model as is electroconvulsive shock (ECS). The test was performed with three subcutaneous injections of EEP, 0.5 mg/kg given immediately after the pre-swim, 5 hours later and one hour before the FST. The pre-swim was conducted 24 hours prior to the FST. A reduced value indicates swim immobility. See table below.

| Swim immobility results (second, means ± SEM): | | |
|---|---|---|
| | (dosage and mode) | |
| | 0.5 mg/kg s.c. | 0.05 mg/kg i.p. |
| Saline | 170 ± 18, n = 12 | 208, n = 11 |
| EEP | 57 ± 15, n = 12 | 121, n = 11 |

$p < 0.001$, 2-way ANOVA (for both conditions)

The results indicate that EEP is highly effective at a low dose. Ogawa et al, Peptides, 5: 743–746 (1984) showed reduced immobility in the same Porsolt FST with 2 and 10 mg/kg of TRH ($p<0.01$, n=8), but no effect with 1 mg/kg.

The same swim test results were subsequently obtained with only 0.05 mg/kg EEP given intraperitoneally (see table above). As a result, EEP may be as much as forty times more potent than TRH in this antidepression model. One of the possible reasons for this result is the relatively short half-life of TRH in the blood. The biological half-life of EEP in blood is at least 7.5 fold greater than TRH. EFP (pyroglutamyl-phenylalanyl-prolyl amide) has an effect similar to EEP on the FST, but is less potent. EFP is also a naturally occurring biological, found in blood, but is synthesized outside the central nervous system.

Example 2

Figure 2:
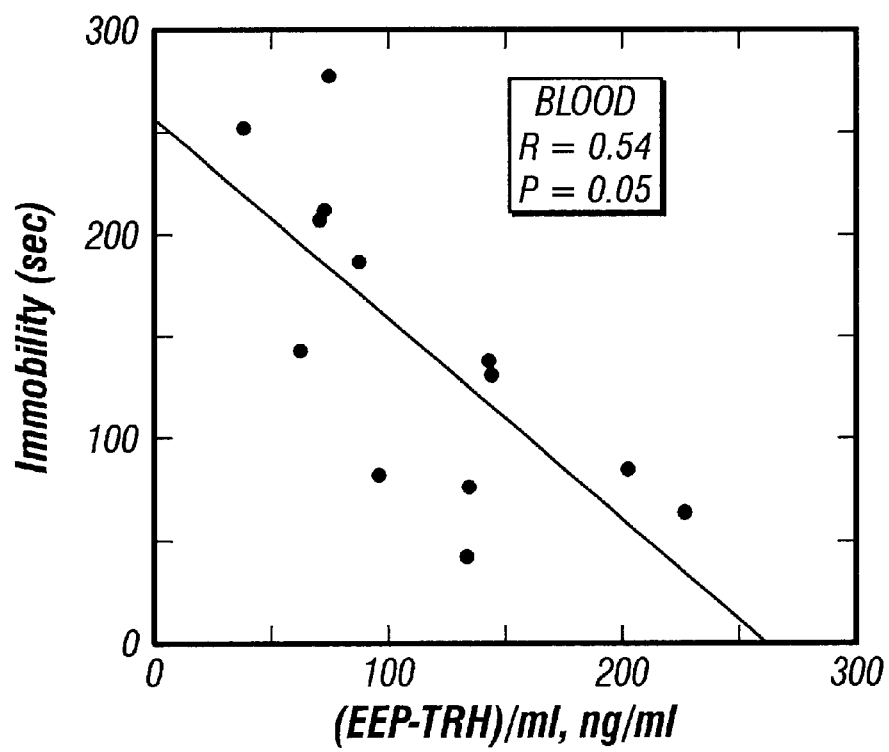
FIG. 2 is a graph showing the correlation of forced swim activity with blood EEP levels in control and ECS-treated rats.

In the same experiment, EEP levels were determined from freshly dissected brain tissue of male Wistar rats that had previously performed the forced-swim test after treatment with electroconvulsive shocks "ECS"). One ECS treatment was given on each of three successive days. The current doses on each of the three successive days were 9.43, 23.5, and 33.0 millicoulombs. This graded increase in current-dose mimics the clinical application of ECT. Their effect on swim immobility time in the Porsolt forced swim test was measured 24 hours after the last ECS. Rats were decapitated and 1.0 ml of whole blood was mixed with 10 ml of methanol on ice and vortex mixed. After centrifugation, the supernatants were transferred to glass test tubes and dried separately. Dried samples from a given experiment were stored at −20° C. and reconstituted with 1.0 ml 0.02% NaN$_3$ prior to EEP and TRH radioimmunoassay (RIA). The results confirmed that there was more EEP than TRH in the key limbic and cortical regions of the brain, and like TRH and related peptides, EEP levels correlated with the degree of swimming following the three ECSs. More significantly, the EEP level in the blood of the ECS rats was significantly higher by two-fold, and the swim scores of all the rats in that study were significantly correlated with the blood level of EEP. See FIG. 2, which plots EEP levels in blood versus swim mobility. Thus, it was shown that one can use the blood levels of EEP in patients as a test for depression and/or a means of assessment of progress in antidepressant treatment.

Example 3

In this experiment, a single corneal electroconvulsive shock ("ECS") was given to 9 rats (versus 6 sham ECS) on each of three successive days following the initial pre-swim, then FST performed 24 hours and sacrifice 48 hours after the third (final) ECS. The ECS currents on each of the three successive days were: 9.43, 23.5, and 33.0 millicoulombs (ramped paradigm). Results are displayed in Table 1, which shows correlations between EEP and swim score, and between TRH and swim score in each of the six brain regions and in blood.

TABLE 1

Correlations (r) and significance (p) of EEP and TRH versus forced-swim test in individual rats for six brain regions.

|  | Ant Ctx | Pyr Ctx | Ay/Entor | Hippoc | Striatum | Mtr Ctx | Blood |
|---|---|---|---|---|---|---|---|
| EEP | | | | | | | |
| r = | 0.173 | 0.548 | 0.361 | 0.849 | 0.557 | 0.671 | 0.735 |
| p < | ns | 0.05 | ns | 0.01 | 0.05 | 0.01 | 0.01 |
| TRH | | | | | | | |
| r = | 0.283 | 0.600 | 0.640 | 0.781 | 0.2 | 0.36 | |
| p < | ns | 0.02 | 0.01 | 0.01 | ns | ns | ns |

(n=6 sham ECS+9 ECS for brain regions and n=6 sham ECS+7 ECS for blood). All peptide levels in these two tables are negatively correlated with immobility (i.e., the higher the peptide level, the lower the immobility score, and the more the rat swims.)

Table 2 presents the effect of the 3 ECS on TRH and EEP levels in the six brain regions.

The effect of three daily transcorneal ECS on the levels of TRH (ng/g wet weight) and EEP (ng/g wet weight) in various brain regions.

TABLE 2

|  | AY | HC | PYR | AC | STR | MC |
|---|---|---|---|---|---|---|
| Control EEP (6) | 2.31 ± 0.76 | 0.42 ± 0.10 | 0.96 ± 0.28 | 0.62 ± 0.33 | 1.35 ± 0.60 | 0.11 ± 0.06 |
| ECS EEP (8) | 3.46 ± 1.14* | 5.15 ± 1.01** | 1.74 ± 0.58** | 0.59 ± 0.22 | 1.64 ± 0.57 | 0.28 ± 0.12** |
| t test | 2.16 | 11.17 | 3.06 | 0.21 | 0.94 | 3.19 |
| Control TRH (6) | 1.45 ± 0.25 | 0.14 ± 0.04 | 0.30 ± 0.10 | 0.17 ± 0.15 | 0.56 ± 0.21 | 0.03 ± 0.01 |
| ECS TRH (9) | 2.53 ± 0.35** | 2.77 ± 0.79** | 1.1 ± 0.33** | 0.15 ± 0.06 | 0.68 ± 0.28 | 0.06 ± 0.03 |
| t test | 6.56 | 7.97 | 5.10 | 0.36 | 0.88 | 1.91 |

EEP was measured by RIA using a rabbit antibody which cross-reacts equally with EEP and TRH. The EEP level (ng/g wet weight) was calculated as the difference between the EEP RIA results (EEP+TRH) and the TRH RIA result (TRH only) in 5 brain regions: amygdala (AY), hippocampus (HC), pyriform cortex (PYR), anterior cortex (AC) and striatum and motor cortex (MC). EEP and TRH levels were highly correlated (p<0.01) in all brain regions except the AC.

In the three major limbic regions, pyriform (olfactory) cortex, amygdala/entorhinal cortex and hippocampus, ECS significantly increased EEP as well as the expected increase in TRH. In striatum, where ECS is known not to increase TRH, EEP was also not increased. In motor cortex, EEP was also increased but the increase in TRH was not significant. However, both peptides were lowest in this region, where TRH has previously been shown to be the lowest among these selected regions. The findings in anterior cortex were atypical with these particular rats in that ECS has no effect on mean level of TRH (nor on EEP). ECS increased EEP in blood, but did not increase TRH in blood.

When EEP is used as a drug with the forced-swim test in rats, it exhibits positive antidepressant effects similar to all proven antidepressants and ECS (ECT). As an example, this test indicated that EEP was forty-fold times more potent than TRH as an antidepressant. This significant increase in potency is explained by the dramatic increase of the half-life of EEP in rat blood as compared to TRH. The half-life of EEP in rat blood is several hours, compared to one minute for TRH. It is believed that the middle glutamate of EEP renders it non-metabolizable by the PAP II enzyme that is the major pathway for the metabolism of TRH.

Example 4

Figure 3:
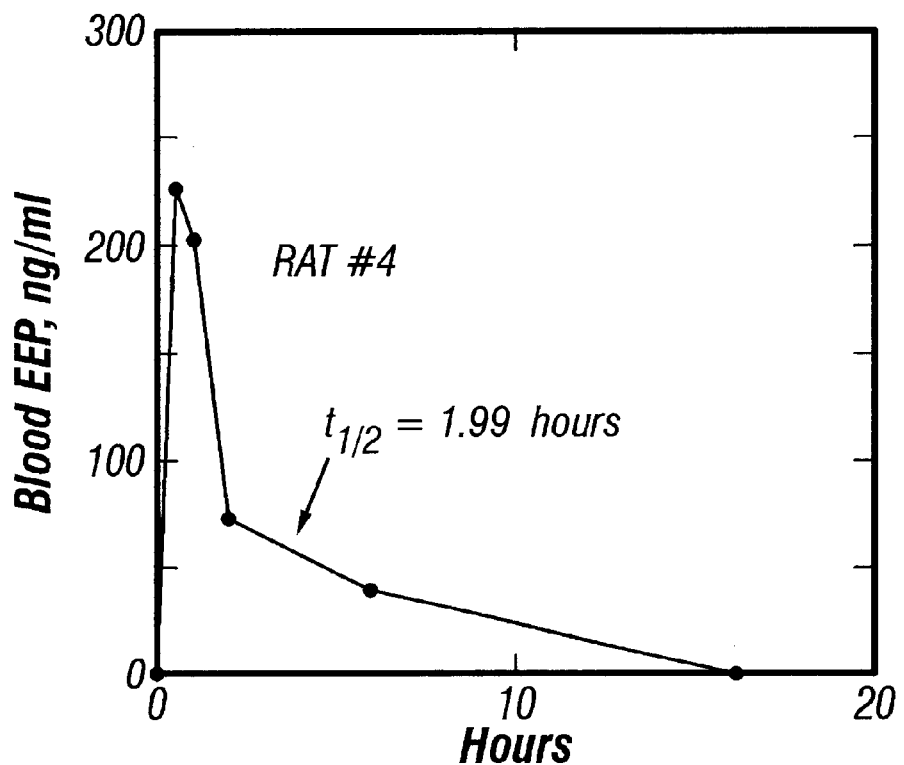
FIG. 3 is a graph showing a representative time course of blood EEP in response to ip injection of 1 mg EEP/kg body weight in two male Sprague-Dawley rats.
Figure 3:
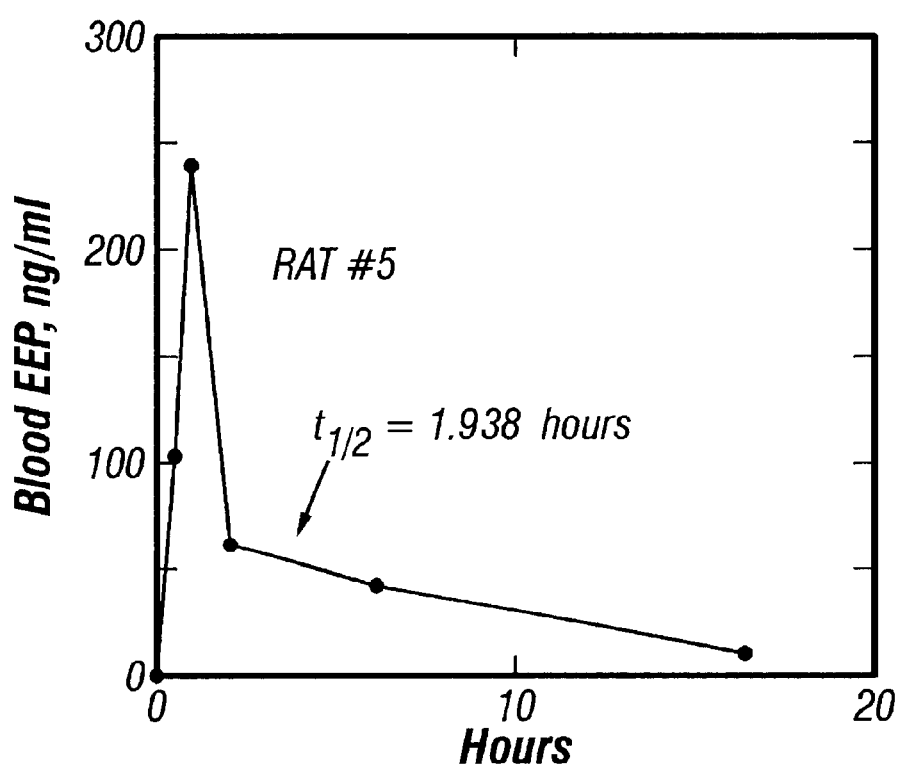
Figure 4:
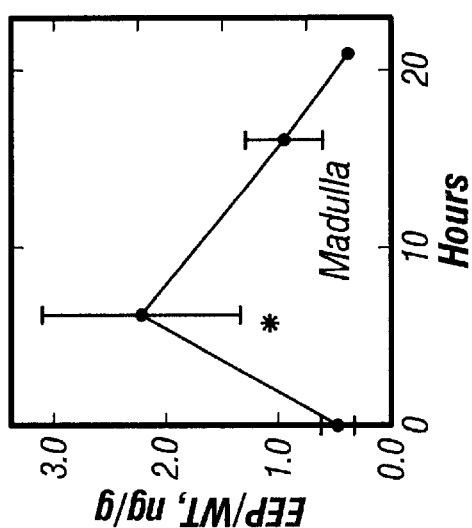
FIG. 4 is a graph showing the time course of tissue EEP levels following ip injection of 1 mg EEP/kg body weight in male Sprague-Dawley rats (two rats were sacrificed at 0, 6, 16 and 21 hours after EEP injection).
Figure 4:
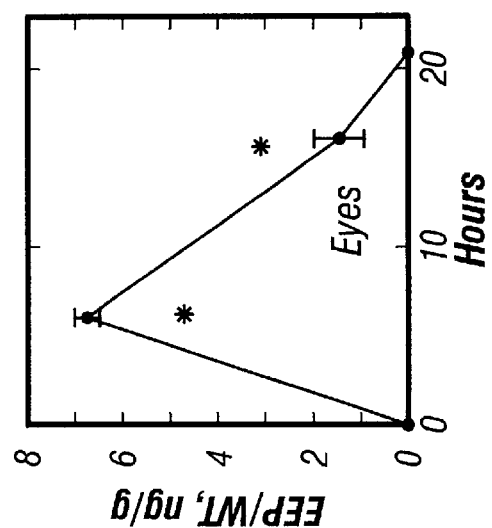
Figure 4:
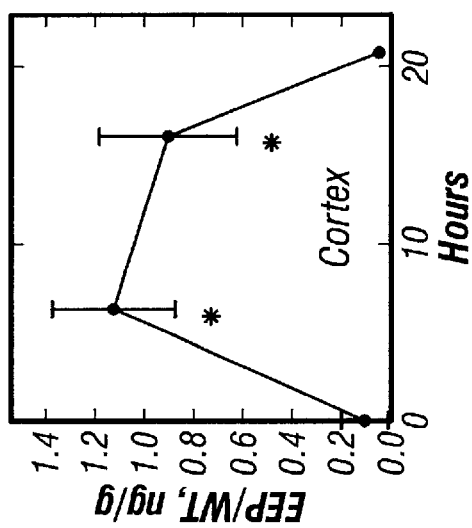
Figure 4:
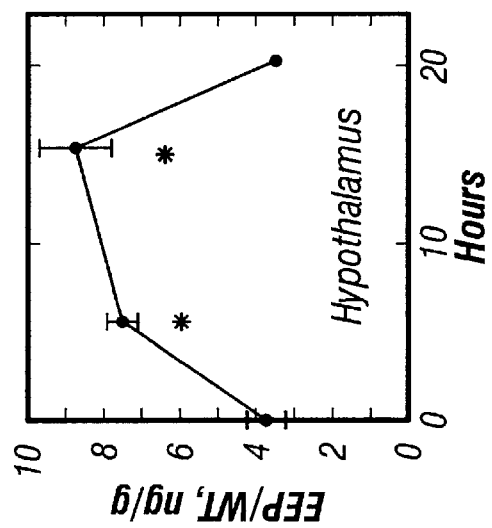
Figure 4:
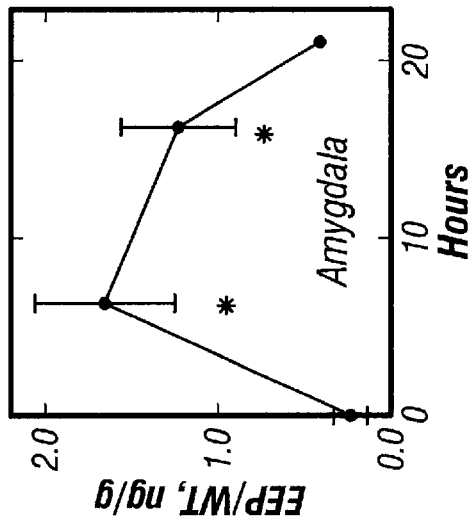
Figure 4:
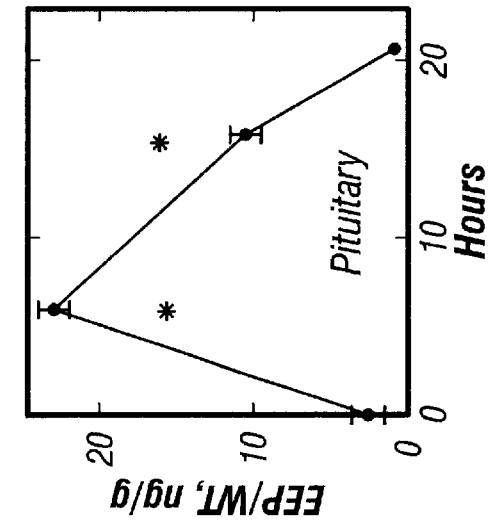

One experiment utilized ip injection of 1.0 mg EEP/kg body weight into rats. This resulted in peak blood EEP at 2 hours, with an average half-life of 2.0 hours. See FIG. 3, representing the time course of blood EEP. Peak brain concentrations of EEP followed, with a range of 6–16 hours in the 6 different regions. See FIG. 4 for the time course of EEP in the brain regions. These results indicate high sustained levels of EEP in the brain, which may result in prolonged antidepressant effects. Because EEP is endogenous to the CNS, rapidly crosses the blood-brain barrier, and is not degradable by serum enzymes, it constitutes a new class of antidepressants.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of treatment of depression, schizophrenia or affective disorders in a mammal comprising the following steps:

a) providing a therapeutically effective amount of a composition comprising a peptide or pharmaceutically acceptable salt thereof of the formula pGlu-Glu-Pro-NH$_2$;

b) administering the composition to the mammal.

2. The method of claim of claim 1, wherein the composition further comprises a pharmaceutically acceptable carrier.

3. The method of claim 1, wherein administering comprises administering by a method of administration selected from the group consisting of oral administration, parenteral administration, transcutaneous administration, intranasal administration and rectal administration.

4. A method of treatment of depression, schizophrenia or affective disorders in a mammal comprising the following steps:

a) providing a therapeutically effective amount of a composition comprising a peptide or pharmaceutically acceptable salt thereof of the formula pGlu-Phe-Pro-NH$_2$;

b) administering the composition to the mammal.

5. The method of claim of claim 4, wherein the composition further comprises a pharmaceutically acceptable carrier.

6. The method of claim 4, wherein administering comprises administering by a method of administration selected from the group consisting of oral administration, parenteral administration, transcutaneous administration, intranasal administration and rectal administration.

* * * * *